United States Patent [19]

Karger et al.

[11] Patent Number: 5,112,460
[45] Date of Patent: May 12, 1992

[54] HIGH PERFORMANCE MICROCAPILLARY GEL ELECTROPHORESIS

[75] Inventors: Barry L. Karger, Newton; Aharon S. Cohen, Brookline, both of Mass.

[73] Assignee: Northeastern University, Boston, Mass.

[21] Appl. No.: 421,609

[22] Filed: Oct. 13, 1989

Related U.S. Application Data

[63] Continuation-in-part of Ser. No. 359,728, May 31, 1989, which is a continuation of Ser. No. 921,311, Oct. 21, 1986, Pat. No. 4,865,706.

[51] Int. Cl.⁵ .................... G01N 27/26; B01D 57/02
[52] U.S. Cl. ............................ 204/182.8; 204/299 R
[58] Field of Search ............. 204/299 R, 183.3, 182.9, 204/182.8

[56] References Cited

U.S. PATENT DOCUMENTS

| | | | |
|---|---|---|---|
| 2,748,074 | 5/1956 | Davis et al. | 204/299 |
| 4,415,428 | 11/1983 | Nochumson et al. | 204/299 |
| 4,533,307 | 8/1985 | Arsorge | 204/299 R |
| 4,690,749 | 9/1987 | Van Alstine et al. | 204/299 |
| 4,747,919 | 5/1988 | Anderson | 204/182.8 |
| 4,865,706 | 9/1989 | Karger et al. | 204/182.8 |
| 4,865,707 | 9/1989 | Karger et al. | 204/182.8 |

FOREIGN PATENT DOCUMENTS

| | | | |
|---|---|---|---|
| 0272925 | 6/1988 | European Pat. Off. | |
| 61114155 | 5/1986 | Japan | 204/182.8 |
| 1233907 | 6/1971 | United Kingdom | |

OTHER PUBLICATIONS

S. Hjerten, "High-Performance Electrophoresis: The Electrophoretic Counterpart of High-Performance Liquid Chromatography", *Journal of Chromatography*, 270 (1983), 1–6.

B. J. Radola, "Ultra-Thin-Layer Isoelectric Focusing", Electrophoretic Techniques (1983), Academic Press, London.

"Partitioning and Electrophoresis in Flexible Polymer Networks", H. J. Bode, Electrophoresis, '79, ©1980 Walter de Gruyter & Co., pp. 39–52.

"Electrophoresis of Proteins and Nucleic Acids on Acrylamide-Agarose Gels Lacking Covalent Cross-linking", Horowitz et al., Analytical Biochemistry 143, 333–340 (1984).

"The Use of Liquid Polyacrylamide in Electrophoresis", H. J. Bode Analytical Biochemistry 83, pp. 204–210 (1977).

"Electrophoresis on Uncrosslinked Polyacrylamide: Molecular Sieving and Its Potential Applications", Tietz et al., Electrophoresis, 1986, 7, pp. 217–220.

*Primary Examiner*—John F. Niebling
*Assistant Examiner*—John S. Starsiak, Jr.
*Attorney, Agent, or Firm*—Weingarten, Schurgin, Gagnebin & Hayes

[57] ABSTRACT

A microcapillary column for high performance electrophoresis. A preferred column includes a microcapillary, a thin layer of coating material covalently bonded to the inner surface of the microcapillary wall, and a gel comprising polyacrylamide polymerized in the tube, filling it. The gel-containing microcapillary is prepared by covalently bonding a layer of a suitable coating material to the inner surface of the microcapillary wall, and then causing a mixture of monomer with or without cross-linking agent, initiator, and polymerization catalyst to react in the bore of the microcapillary to form a polymeric matrix. In electrophoresis, the gel-containing microcapillary provides peak efficiencies in excess of 100,000 theoretical plates and in some instances over 1,000,000 theoretical plates within separation times of less than thirty minutes, permits trace level determinations of molecular weights, and permits electrophoretic operation at fields of 300 V/cm or higher, resulting in extremely high resolution separations.

7 Claims, 10 Drawing Sheets

HIGH PERFORMANCE MICROCAPILLARY GEL ELECTROPHORESIS

CROSS-REFERENCE TO RELATED APPLICATION

This is a continuation-in-part of application Ser. No. 07/359,728, filed May 31, 1989, which is hereby incorporated by reference. Application Ser. No. 07/359,728 is a continuation of parent application Ser. No. 06/921,311, filed Oct. 21, 1986, now U.S. Pat. No. 4,865,706. A related application is Ser. No. 07/143,442, filed Jan. 12, 1988, which is another continuation-in-part application based on the same parent application. A second related application is Ser. No. 07/406,080, now U.S. Pat. No. 4,997,537, filed Sep. 12, 1989, which is another continuation-in-part application based on application Ser. No. 07/359,728.

FIELD OF THE INVENTION

This invention relates to electrophoresis, and more particularly, to gel-containing microcapillary colunms for high performance analytical electrophoresis.

BACKGROUND OF THE INVENTION

Electrophoresis is one of the most widely used separation techniques in the biologically-related sciences. Molecular species such as peptides, proteins, and oligonucleotides are separated by causing them to migrate in a buffer solution under the influence of an electric field. This buffer solution normally is used in conjunction with a low to moderate concentration of an appropriate gelling agent such as agarose or polyacrylamide to minimize the occurrence of convective mixing.

Two primary separating mechanisms exist, separations based on differences in the effective charge of the analytes, and separations based on molecular size The first of these mechanisms is limited to low or moderate molecular weight materials in the case of separations of oligonucleotides because in the high molecular weight range the effective charges of these materials become rather similar, making it difficult or impossible to separate them. In the case of proteins, charge and size can be used independently to achieve separations. Separations based on molecular size are generally referred to as molecular sieving and are carried out employing as the separating medium gel matrices having controlled pore sizes. In such separating systems, if the effective charges of the analytes are the same, the separation results from differences in the abilities of the different sized molecular species to penetrate through the gel matrix. Smaller molecules move relatively more quickly than larger ones through a gel of a given pore size. Oligonucleotides and medium to high molecular weight polypeptides and proteins are commonly separated by molecular sieving electrophoresis. In the case of proteinaceous materials, however, it is first generally necessary to modify the materials to be separated so that they all have the same effective charges. This is commonly done by employing an SDS-PAGE derivatization procedure, such as is discussed in "Gel Electrophoresis of Proteins," B. D. Hames and D. Rickwood, Eds., published by IRL Press, Oxford and Washington, D.C., 1981. The contents of this book are hereby incorporated herein by reference.

Sometimes it is desirable to separate proteinaceous materials under conditions which pose a minimal risk of denaturation. In such cases system additives such as urea and SDS are avoided, and the resulting separations are based on differences in both the molecular sizes and charges.

Most electrophoretic separations are today conducted in slabs or open beds. However, such separations are hard to automate or quantitate. Extremely high resolution separations of materials having different effective charges have been achieved by open tubular free-zone electrophoresis and isotachophoresis in narrow capillary tubes. In addition, bulk flow can be driven by electroosmosis to yield very sharp peaks. Such high efficiency open tubular electrophoresis has not generally been applied to the separation of medium to high molecular weight oligonucleotides, however, since these materials have very similar effective charges, as indicated above. In addition, open tubular electrophoresis does not provide size selectivity for proteinaceous materials. The questions thus arise whether electrophoresis on gel-containing microcapillaries can be employed to achieve high resolution separations of oligonucleotides, and whether the conventional procedure of SDS-PAGE can be accomplished on such microcapillaries. As demonstrated by the present disclosure, the answers to these questions are affirmative, although given its potential importance as a separating technique in the biological sciences, surprisingly little attention has been paid to microcapillary gel electrophoresis.

Hjerten has published an article in the *Journal of Chromatography*, 270, 1–6 (1983), entitled "High Performance Electrophoresis: The Electrophoretic Counterpart of High Performance Liquid Chromatography," in which he employs a crosslinked polyacrylamide gel in tubes having inside dimensions of 50–300 micrometers, and wall thicknesses of 100–200 micrometers. However, this work suffers from limited efficiency and relatively poor performance due in part to the use of relatively wide bore capillaries, relatively low applied fields, high electrical currents, and insufficient suppression of electroendosmosis. He has also obtained U.S. Pat. No. 3,728,145, in which he discloses a method for coating the inner wall of a large bore tube with a neutral hydrophilic substance such as methyl cellulose or polyacrylamide to reduce electroendosmosis in free-zone electrophoresis in open tubes. In a later U.S. Pat. No. 4,680,201, Hjerten discloses a method for coating the inner wall of a narrow bore capillary with a monomolecular polymeric coating of polyacrylamide bonded to the capillary wall by means of a bifunctional reagent. These capillaries are also open tubes to be used for free-zone electrophoresis.

The small amount of work in the field of gel electrophoresis in capillaries by researchers other than the present applicants has generally resulted in columns which were not highly stable and could not be subjected to sufficiently high electric fields to achieve high efficiencies and high resolution separations. Improved gel-filled capillary columns for electrophoresis which provide superior stability, efficiency, and resolution would be of great value in bioanalytical chemistry.

SUMMARY OF THE INVENTION

The above-identified need for stable and efficient gel-filled capillary electrophoresis columns is answered by the present invention, which provides an improved gel-containing microcapillary for high performance electrophoresis. It includes a microcapillary, a polymeric gel in the interior cavity of the microcapillary, and a thin layer of coating material covalently bonded to the inner surface of the microcapillary wall and preferably also bonded to the polymeric gel.

The layer of coating material between the microcapillary wall and the layer of hydrophilic polymer is generally a hydrophobic material and originates as a reagent possessing a reactive functional group capable of reacting with reactive functionalities on the interior surface of the capillary wall, silanol groups, for example. The remainder of the reagent may include a second reactive group which is capable in principle of reacting with vinyl monomers and optional crosslinking agents which when polymerized constitute the polymeric gel.

The improved gel-containing microcapillary of the invention is prepared as follows: first, the interior surface of a microcapillary is activated by contacting it with a basic material, or an acidic material, or both in sequence, then it is treated with a solution of an appropriate coating reagent capable of covalent bonding to the microcapillary wall, resulting in formation of a layer of the coating material covalently attached to the inner surface of the microcapillary wall. Following this operation, the microcapillary is filled with a solution containing at least one monomer, and optionally at least one crosslinking agent, plus at least one free radical source and an appropriate catalyst, and this mixture is allowed to polymerize in the tube, ultimately forming a polymeric matrix which fills the capillary bore. As a final step, one end of the gel-containing microcapillary is cut off cleanly and squarely.

The gel-containing microcapillaries of the invention are unusually stable and function well under applied electric fields typically of 300 volts/cm or higher, and with currents typically up to approximately 50 microamperes or above. Under these conditions, extremely high resolution separations are obtained on very small amounts of material. In addition, the microcapillaries of the invention have been demonstrated to resolve mixtures of analytes as a linear function of the logarithms of their molecular weights. Accordingly, they permit convenient and accurate molecular weight determinations on nanogram or lower amounts of unknown biopolymers.

DESCRIPTION OF THE DRAWING

The invention will be better understood from a consideration of the following detailed description taken in conjunction with the drawing in which.

DETAILED DESCRIPTION OF THE INVENTION

Figure 1:
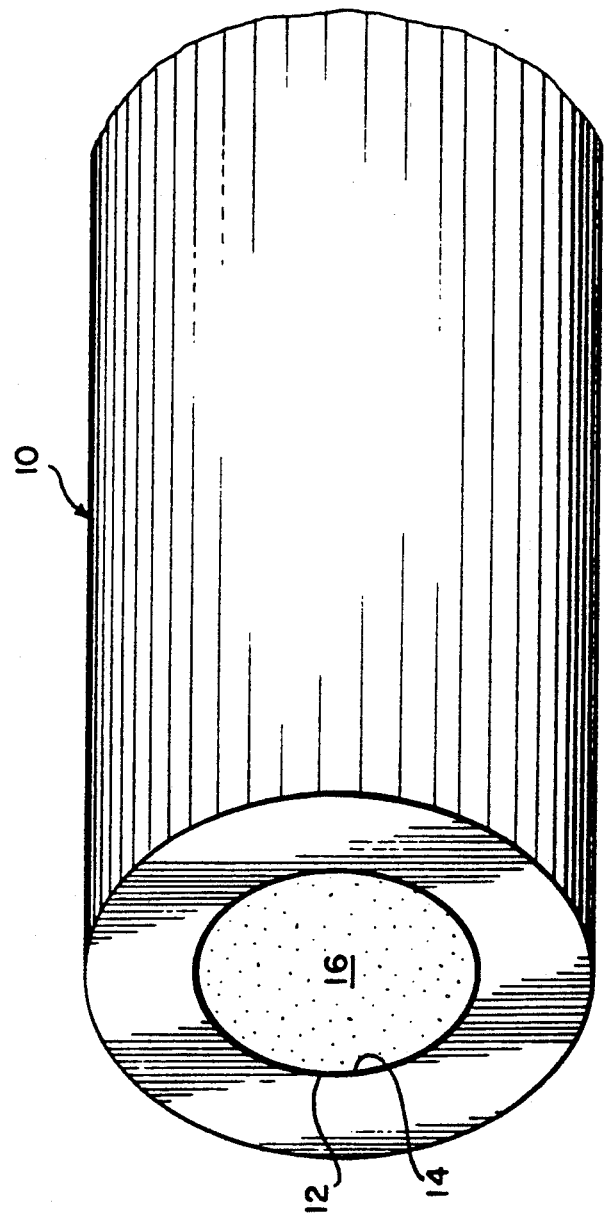
FIG. 1 shows a magnified perspective view of the end of the gel-containing microcapillary of the invention.

As shown in FIG. 1, the gel-containing microcapillary column of the invention includes a microcapillary 10, a layer 12 of coating material which is covalently bonded to the inner surface 14 of the microcapillary wall, and a polymeric gel material 16 within the bore of this microcapillary.

As employed herein, the term "polymeric gel" means a three-dimensional network of polymer chains held together by any of a variety of means such as covalently bonded crosslinking units, long range attractive forces, hydrogen bonds, entanglement of the molecular chains, etc., and dispersed in a liquid phase. The polymeric network provides sufficient structure for a degree of rigidity, and other components of the system occupy the spaces between the polymeric chains.

The microcapillary may be made of any of a variety of materials provided that the detection system to be employed in the electrophoresis can function adequately with the particular material employed. Suitable materials include glass, alumina, beryllia, and TEFLON. Preferably, the microcapillary is made of fused silica.

The microcapillary dimensions are important because, for a given electric field, as the internal diameter of the microcapillary is reduced, the electric current and the resultant heating produced by a particular applied electric field is reduced. Thus, for highest resolution separations it is desirable that the microcapillary have a minimum internal diameter. With the improved microcapillaries of this invention, however, this factor is somewhat less important than formerly. Accordingly, microcapillaries having internal diameters in the range between 10 and 2000 micrometers function in the invention. A preferred range of internal diameters is 10 to 200 micrometers. A polyimide coating on the outer surface of the microcapillary permits easy handling of thin-walled microcapillaries.

The polymeric gel material 16 employed can be any polymer which has a pore structure which can be varied. It may or may not be crosslinked. Preferably, the polymeric gel is a crosslinked polymer whose pore structure is varied by varying the amounts of monomer and crosslinking agent, and the reaction conditions. Examples of suitable polymeric systems are polyacrylamide, agarose, and mixtures of agarose and polyacrylamide. A preferred polymeric gel material is based on acrylamide and N,N'-methylenebisacrylamide, the N,N'-methylenebisacrylamide serving as a crosslinking agent. Other possible crosslinking agents are N,N'-(1,2-dihydroxyethylene)-bisacrylamide, N,N'-diallyltartardiamide, and N,N'-cystamine-bisacrylamide. Still other monomers and crosslinkers will suggest themselves to those skilled in the art.

The polymerization reaction is preferably initiated with ammonium persulfate or N,N,N',N'-tetramethyleneethylenediamine, though other free radical polymerization initiators may be employed, as known by those skilled in the art.

The layer 12 between the polymeric gel 16 and the inner surface 14 of the microcapillary wall is generally a hydrophobic material and is derived from a coating reagent which is capable of chemically bonding to the microcapillary wall. This reagent is generally a molecular chain having an appropriate reactive functional group at one end, though non-chain type molecules having appropriate functionalities will also serve. The end of the coating reagent which is to bond to the capillary wall carries a reactive functional group which can bond chemically to silanol groups or other reactive functionalities on the inner surface of the microcapillary. Such reactive functional groups of the reagent are typically reactive silanes such as trialkoxysilane, trichlorosilane, mono, di-, or tri-enolate silanes, and aminosilanes, where the silicon atom carries at least one group which may be readily displaced. Examples of suitable coating reagents are materials such as alkyl di- or tri- ethoxy or methoxy silanes, and alkylether di- or tri- ethoxy or methoxy silanes.

In a preferred embodiment, the coating reagent is a bifunctional material, which also contains a second functional group capable in principle of forming a covalent bond with the polymeric gel material. Such functional groups include vinyl, substituted vinyl, or any group which upon cleavage yields a free radical, but for practical purposes a vinyl group is preferred because it is then possible to form the polymeric gel in the microcapillary and chemically bond it to the microcapillary wall simultaneously. Representative bifunctional reagents are 3-Methacryloxypropyl-trimethyoxysilane, and 3-Methacryloxypropyldimethylethoxysilane, shown as a) and b) below:

a) $CH_2=C(CH_3)-CO_2-(CH_2)_3-Si(OCH_3)_3$
b) $CH_2=C(CH_3)-CO_2-(CH_2)_3-Si(CH_3)_2OC_2H_5$.

Other possible bifunctional reagents are vinyltriacetoxysilane, vinyltri( -methoxyethoxy)silane, vinyltrichlorosilane, and methylvinyldichlorosilane, this list being intended as illustrative but not exhaustive.

In the case of capillaries to which the bifunctional reagents do not bond, e.g., TEFLON, the capillaries may be employed without a coating layer 12, or a layer of a polymer possessing the ability to adsorb to the microcapillary wall and to the polymeric gel may be employed.

For highest resolution it is necessary that at least the front end of the gel-containing microcapillary be cleanly and squarely cut perpendicular to the central axis of the microcapillary. If the surface of the polymeric gel material which is exposed at the end of the microcapillary is uneven, it is impossible to make an injection of a uniform narrow band of sample, with the result that broad peaks are obtained.

The gel-containing microcapillaries of the invention are generally prepared as follows. First, the column is activated by heating it in excess of 100° C., generally for several hours, and then bringing its interior surface into contact with an acidic material such as a dilute solution of hydrochloric or nitric acid, and/or a basic material such as ammonia gas or a solution of a base. In the heating step a temperature of 110° to 200° C. may be conveniently employed. The time of such heating can vary from a few hours to overnight or longer. In one procedure, the activating step is accomplished by flushing the microcapillary with dry ammonia gas, generally for approximately 2 hours at a temperature of approximately preferred procedure, the column may be activated by heating it as above, then filling it with a solution of a base such as an alkali metal hydroxide, e.g., an 0.1 to 1N NaOH solution, approximately 1-3 hours and conveniently overnight at a temperature typically in the range 20°-35° C., preferably at room temperature, then flushing with water.

The time and temperature employed in activating the microcapillary are selected such that they are sufficient to activate the microcapillary so that good bonding between the microcapillary and the bifunctional reagent is achieved.

The activated microcapillary is then flushed with at least 20 tubing volumes of a solution of the reagent to be employed in coating the tubing wall, and this is left to react for at least 1 hour and preferably 2 hours or longer at a temperature of 20°-35° C., preferably at room temperature, filled with this solution of coating reagent. An alternative procedure is to place the filled microcapillary column in a vacuum oven overnight at about 60° C.

The solution of coating reagent is prepared in a nonaqueous solvent such as an alcohol, an ether, a ketone, or a moderately polar halogenated solvent and typically contains between 4 and 60% coating reagent by volume. Representative solvents are methanol, dioxane, acetone, and methylene chloride. After the coating reagent has been allowed to react with the inner wall of the microcapillary, excess unreacted reagent is optionally removed by rinsing the column with a suitable solvent such as methanol, followed by a further rinsing with water. Typically at least 100 tubing volumes of solvent and water are employed.

Next, separate stock solutions of the monomers, any cross-linkers, the initiators, and free radical sources for the polymerization reaction are prepared, typically in 7 to 8 molar aqueous urea, though higher and lower concentrations of urea may be used. Gels which are intended to be non-denaturing are prepared without urea or other denaturing additives, and function well. The concentrations of these reagents are selected such that convenient aliquots of the solutions may be taken and mixed together to form a polymerization mixture having predetermined concentrations of monomer, cross-linker (if employed), and polymerization catalysts. Before mixing aliquots of these reagents together, the solutions are separately degassed for at least one hour. This degassing operation may be conducted in any of the several ways known to the art, but basically involves stirring the solutions mechanically or agitating them with ultrasound while simultaneously applying a low vacuum of approximately 20 to 30 millimeters of mercury. The preparation of these solutions is as known to the art, for example, as shown by Hames and Rickwood.

The total concentration of monomer and the concentration of crosslinking agent in these sorts of systems are generally expressed respectively as % T and % C, employing the terminology of Hjerten. In this regard, see Hjerten, Chromatographic Reviews, 9, 122–219 (1967). For the acrylamide N,N'-methylenebisacrylamide system preferably employed in this invention, the definitions of % T and % C are given below.

$$\% \ T = \frac{\text{grams of acrylamide} + \text{grams of bisacrylamide}}{100 \text{ milliliters of solvent}}$$

$$\% \ C = \frac{\text{grams of bisacrylamide} \times 100}{\text{grams of bisacrylamide} + \text{grams of acrylamide}}$$

The concentrations of monomer and any crosslinking agent are predetermined according to the porosity of the polymeric matrix desired. However, the concentrations of initiator and polymerization catalyst in the reaction mixture must be determined experimentally. This is done by preparing test solutions containing the desired % T and % C, but varying the amount of initiator and polymerization catalyst employed. In the event that SDS-PAGE electrophoresis is contemplated, sodium dodecylsulfate is also included in the reaction mixture in the requisite amount, typically 0.1% (w/v). These test solutions are allowed to polymerize at or below the temperature at which the electrophoresis is to be performed and the progress of the polymerization reaction is monitored by ultraviolet spectroscopy by observing the decrease in the absorbance of the vinyl double bond. Alternatively, the microcapillary may be observed visually. Levels of initiator and polymerization catalyst are selected which cause the polymerization of the test mixture to be essentially complete in a reasonable time, such as approximately 45 to 60 minutes.

Once the correct reagent concentrations have thus been determined, a fresh mixture of the polymerization reagents is prepared and injected into the microcapillary tube, taking care not to create bubbles. A small ID TEFLON tube is used to connect the microcapillary to the syringe employed to fill the microcapillary. When the microcapillary has been filled with polymerization mixture, the syringe is removed and both ends of the microcapillary are plugged by inserting them into septa, which are maintained while the polymerization reaction occurs.

The polymerization reaction is carried out at or below the temperature which is to be employed for subsequent electrophoresis on the microcapillary column. While the polymerization reaction is occurring, the reaction may be monitored separately in an aliquot of the reaction mixture by observing the loss of absorbance due to the vinyl groups by ultraviolet spectroscopy or visually. The polymerization reaction in the column and that in the separate monitor solution are the same, although the reaction in the capillary is much faster. When the test solution indicates the polymerization reaction is essentially over, which should be at a time between 45 and 60 minutes, the reaction proceed for at least another two hours, preferably overnight, maintaining the temperature as indicated above.

An alternative and preferred polymerization procedure is to fill the microcapillary column with the solution of polymerization reagents as described above, then immediately place the column in a refrigerator at a temperature of 5°–10° C. and allow the polymerization reaction to proceed overnight.

After the polymerization reaction in the microcapillary has gone essentially to completion, the caps are removed from the microcapillary ends and at least one end of the microcapillary is cut off cleanly and squarely. One way to accomplish this is to tightly sheath an end to be cut with small diameter TEFLON tubing, then cut the TEFLON-sheathed end cleanly and squarely perpendicular to the axis of the microcapillary using a microtome, which cuts through the TEFLON sheathing, the microcapillary material, and the polymeric gel, leaving a very smooth surface of gel material exposed at the end of the microcapillary. Alternatively and preferably, the capillary may be scored carefully at a right angle to its axis be means of a sapphire cleaver, and broken cleanly by bending it. The end of the microcapillary which has been thus cut is examined under a microscope to ascertain that the cutting operation in fact produced the requisite flatness of the exposed polymeric gel. If necessary, further cuts can be made until a suitably flat end is produced. Both ends of the microcapillary are generally treated in this fashion, although it is really only necessary to have a square cut end on the front of the microcapillary.

After its preparation, the column is placed in suitable electrophoresis apparatus and a low electric field of approximately 100 to 150 volts/cm is applied for a period of about one hour. If a very noisy baseline or a zero current condition is obtained, this indicates an improperly prepared column. In this event, a new microcapillary must be prepared.

In employing the gel-containing microcapillary column of the invention in electrophoresis, apparatus and techniques which are generally known to the those skilled in the art of open tube free-zone microcapillary electrophoresis are employed. See, for example, B. L. Karger, A. S. Cohen, and A. Guttman, J. Chromatog. 492, 585 (1989); M. J. Gordon, X. Hung, S. L. Pentaney, Jr., and R. N. Zare, Science, 242, 224 (1988); and J. W. Jorgenson and K. D. Lukacs, Science, 222, 266–272 (1983). In capillary gel electrophoresis, resolution between two compounds is influenced by all the factors which affect band sharpness, including sample size, ionic materials in the samples, and the gel concentration. The latter factor is especially important, since if the gel concentration is too high the analytes are totally excluded from the column, while if it is too low little or no molecular sieving occurs. No single gel concentration is optimal for the resolution of all mixtures of proteinaceous materials or oligonucleotides. It is necessary to select appropriate gel concentrations for particular samples. Other important variables affecting electrophoresis in microcapillaries are the applied field and the electrical current employed. The sample is injected by the so-called "electrophoretic injection" technique, though other techniques known to the art, such as syringe layering injection, can serve. In the electrophoretic injection technique, the front end of the electrophoresis microcapillary is dipped into a sample solution containing an electrode of the appropriate polarity and an electric field of approximately 50 to 100 volts/cm is applied for a few seconds to cause electrophoresis of a small amount of the sample solution into the end of the microcapillary. The microcapillary is then transferred back to a solution of "running" buffer, the desired electrophoretic field is applied, and the electrophoresis is carried out in the normal way.

To aid in cooling the microcapillary, a cooling jacket or a related device is employed around the microcapillary over most of its length, excluding only the front and the rear ends of the microcapillary, which are respectively immersed in buffer solution and connected to the detector of the electrophoretic system. A cooling fluid is circulated through this jacket and maintained at whatever temperature is desired. Alternatively, an electrically controlled mechanical cooling device may be employed around the microcapillary column. Such "active" cooling is more effective in maintaining desired microcapillary temperatures than forced air or natural convection.

A method of performing high resolution molecular sieving electrophoresis for analytical purposes thus includes the steps of electrophoretically injecting an aliquot of a sample containing analytes to be separated into a gel-containing microcapillary column of the invention, applying an electric field of between 100 and 300 volts/cm or higher, allowing a current typically less than about 50 microamperes to pass through the microcapillary, and instrumentally detecting and measuring the separated analytes sequentially as they migrate past the detector.

The gel-containing microcapillaries of the invention separate analytes as a function of the logarithms of their molecular weights in a linear fashion. Accordingly, it is possible to determine molecular weights of unknown analytes by comparing their mobilities under standard electrophoretic conditions with a calibration chart plotting the log of the molecular weight of standard materials versus the mobilities of such standard materials.

A method of determining the molecular weight of an analyte therefore is to prepare a gel-containing microcapillary column according to this invention, select standard values of the electrophoretic operating parameters, the applied field being typically between 100 and 300 volts/cm or higher and the injecting onto this microcapillary column an aliquot of a standard solution containing several standard analytes of known molecular weight, applying the selected standard values of the electrophoretic operating parameters to the microcapillary column to separate the standards, measuring mobilities of the known standards under the conditions of the electrophoresis, plotting the log of the molecular weight for each of the standard materials versus its mobility under the standard operating conditions, electrophoretically analyzing an unknown solution on the same column under the same conditions, measuring the mobilities of the analytes contained therein, and finally determining the molecular weights of these analytes from a comparison with the calibration plot.

The improved microcapillary columns containing a layer of wall coating material between the polymeric gel filling and the capillary wall exhibit longer shelf lives and better stability in use than columns not containing such capillary wall coatings. Most importantly and unexpectedly, the improved microcapillary columns of the invention can be operated at high field strengths, which permit high resolution separations to be achieved in short analysis times.

The following experimental preparations are intended as exemplary only, and are not intended to limit or define the scope of the invention.

EXPERIMENTAL SECTION

Acrylamide, N,N'-methylenebisacrylamide, N,N,N',N'-tetramethyleneethylenediamine (TEMED), ammonium persulfate, sodium dodecylsulfate, TRIS buffer, and disodium hydrogen phosphate were all ultrapure or electrophoretic grade materials obtained from Swartz/Mann Biotech of Cleveland, Ohio. Somewhat less pure acrylamide from other sources could be suitably purified by recrystallizing three times and deionizing it by treatment with ion exchange resin. Urea was freshly obtained, and triply recrystallized from water/methanol. Proteins were obtained from the Sigma Chemical Company, St. Louis, Mo. and used as received. Poly(deoxyadenylic acid) and $\phi$X174RF/HaeIII DNA fragments were obtained from Pharmacia. Water was triply distilled and deionized. The fused silica microcapillary tubing preferably employed in the invention was obtained originally from Scientific Glass Engineering Inc., Austin, Tex., and for later work, from Polymicro Technologies, Inc., Phoenix, Ariz. Polymicro Technologies also supplies such tubing in various other dimensions. A sapphire cleaver useful in cutting off the ends of the microcapillaries was obtained from Ealing Electronics Corp., 22 Pleasant Street, South Natick, Mass. 01760.

Narrow bore TEFLON tubing (0.2–0.25 millimeters ID) was used for filling microcapillary tubes. All solutions were filtered through a nylon 66 or methylcellulose filter membrane having a 0.2 micrometer pore size. Analytical samples were kept frozen at −20° C. prior to use, and aliquots of these samples for experimental work were stored at 4° C. Proteins for SDS-PAGE work were prepared as known to the art.

A Soma S-3207 detector by Instrumentation for Research and Development, Inc., Kingston, Mass., was employed, and was modified for microcapillary work as described in the article by S. Terabe, et al, *Anal. Chem.*, 56, 111-113 (1984). Data were converted to digital form using a Nelson Analytical A/D Interface model 762 SA, and stored using an IBM PC/XT computer. Other equipment known to the art will also serve.

Preparation and Testing of Gel-Containing Microcapillary Having 10% T. 3.3% C. and 0.1% SDS Fused silica microcapillary tubing having an ID of 75 micrometers, a wall thickness of 30 micrometers, and a polyimide coating was employed. A 40 to 45 cm length of this tubing was taken for preparation of the gel-containing microcapillary. The polyimide coating was removed from a 1 cm section of one end of the tubing by burning. This end was ultimately connected to the detector of the electrophoresis apparatus.

The microcapillary tubing was heated overnight at about 120° C. in air, then flushed with dry ammonia gas at about 30° C. for approximately two hours. This and other operations reported herein as being carried out at about 30° C. were conducted at room temperature, which is generally about 3° C.± about 3° C. Next 100 μl of a 50% solution of 3-Methacryloxypropyltrimethyoxysilane in methanol were passed through the microcapillary at a temperature of about 30° C., leaving the microcapillary filled with bifunctional reagent solution, the ends of the microcapillary were connected via a short length of TEFLON tubing (also filled with bifunctional reagent solution), and the closed and reagent-filled microcapillary was left overnight at about 30° C. The TEFLON tubing was then removed from one end of the microcapillary, and the microcapillary was flushed successively with 250 µl each of methanol and water to remove unreacted bifunctional reagent. The coated microcapillary was then installed in the detector of the electrophoresis apparatus, and 15 cm sections of the treated and the untreated microcapillaries were taken for analysis. The treated microcapillary was cut to a length of somewhat greater than 20 cm, and a sheathing of TEFLON was installed on its "front" end.

Buffer solution was prepared by dissolving 1.1 g of TRIS buffer in 100 ml of 7 molar urea solution, adding 0.01 g of EDTA and 0.1 g of sodium dodecyl sulfate, and adjusting the pH to 8.6 by the addition of sodium dihydrogen phosphate.

A solution of acrylamide and N,N'-methylenebisacrylamide was prepared by combining 29 g of acrylamide and 1 g of N,N'-methylenebisacrylamide in 100 ml of buffer solution, giving a solution having a % T of 30% and a % C of 3.3%.

A solution of ammonium persulfate was prepared by dissolving 0.2 g of ammonium persulfate in 2 ml of the buffer solution.

The solutions of buffer, monomers, and ammonium persulfate were separately filtered through 0.2 micrometer filters and degassed for 2 hours by treating them with ultrasound while applying a vacuum of 20–30 mm of mercury.

Ten ml of the acrylamide-bisacrylamide solution was diluted to 30 ml with buffer solution, giving a final solution having % T 10% and % C 3.3%. One ml aliquots of this solution were experimentally treated with varying amounts of ammonium persulfate solution and TEMED, and polymerization times were monitored to determine the correct amounts of persulfate and TEMED to use. It was ascertained that addition of 2.5 µl of TEMED and 4 µl of the persulfate solution gave a polymerization time of about 45 minutes.

A 10 ml aliquot of the acrylamide-bisacrylamide solution was diluted to 30 ml with buffer solution, 2.5 µl of TEMED and 4 µl of ammonium persulfate solution were added, and in excess of 50 µl of this polymerization mixture were forced through the microcapillary until no bubbles were observed exiting the microcapillary. The injection syringe was carefully removed from the TEFLON tubing while continuing the injection, to prevent introduction of bubbles into the microcapillary. Finally, both ends of the microcapillary were immersed in "running" buffer and the polymerization was allowed to proceed at about 30° C. The polymerization of the remainder of the polymerization mixture was externally monitored. After the polymerization appeared complete, the system was left for a further two hours to ensure full polymerization, then the microcapillary front end was cut off in a microtome at a microcapillary migration distance (front end to detector) of 20 cm. The final gel-containing microcapillary was evaluated for one hour under an applied field of 100 volts/cm, and found to be satisfactory.

Figure 2:
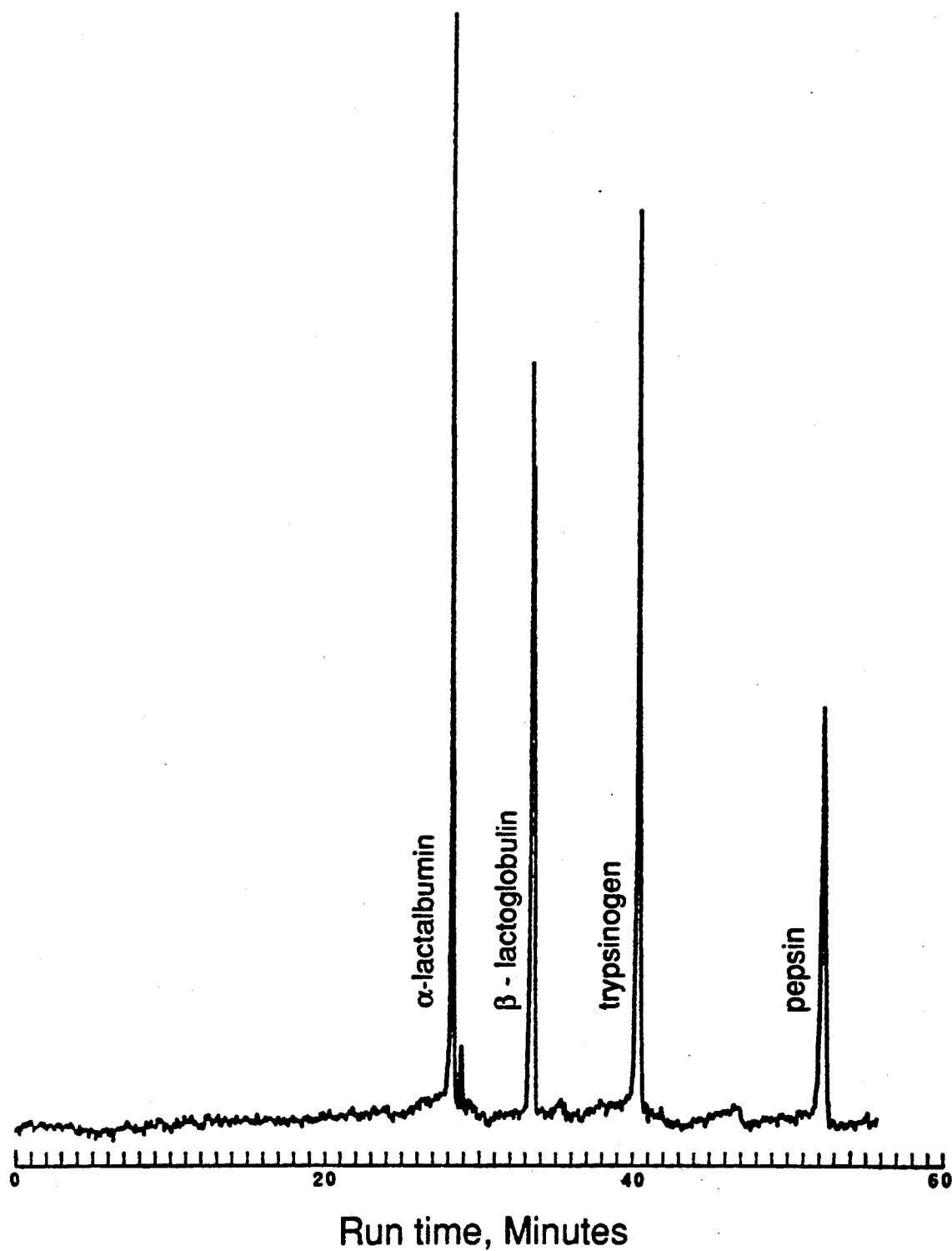
FIG. 2 shows an electropherogram of four standard proteins, $\alpha$-lactalbumin, $\beta$-lactoglobulin, trypsinogen, and pepsin on a gel-containing microcapillary column of the invention containing 10% total monomer, 3.3% crosslinker, and 0.1% SDS. The PH of the buffer was 8.6, and electrophoresis was conducted under an applied field of 400 volts/cm and a current of 24 microamperes, over a 20 centimeter migration distance.

A mixture of four proteins, α-lactalbumin, β-lactoglobulin, trypsinogen, and pepsin, was prepared for SDS-PAGE electrophoresis in the standard manner known to the art, then a sample of this solution was electrophoretically injected onto the microcapillary column by application of an electrical field of 100 volts/cm for 15 seconds. Electrophoresis was conducted at 400 volts/cm and a current of 24 µA over the 20 cm migration distance. Results are shown in FIG. 2.

Preparation and Testing of Gel-Containing Microcapillaries Having % T=7.5 and 5%

Figure 3:
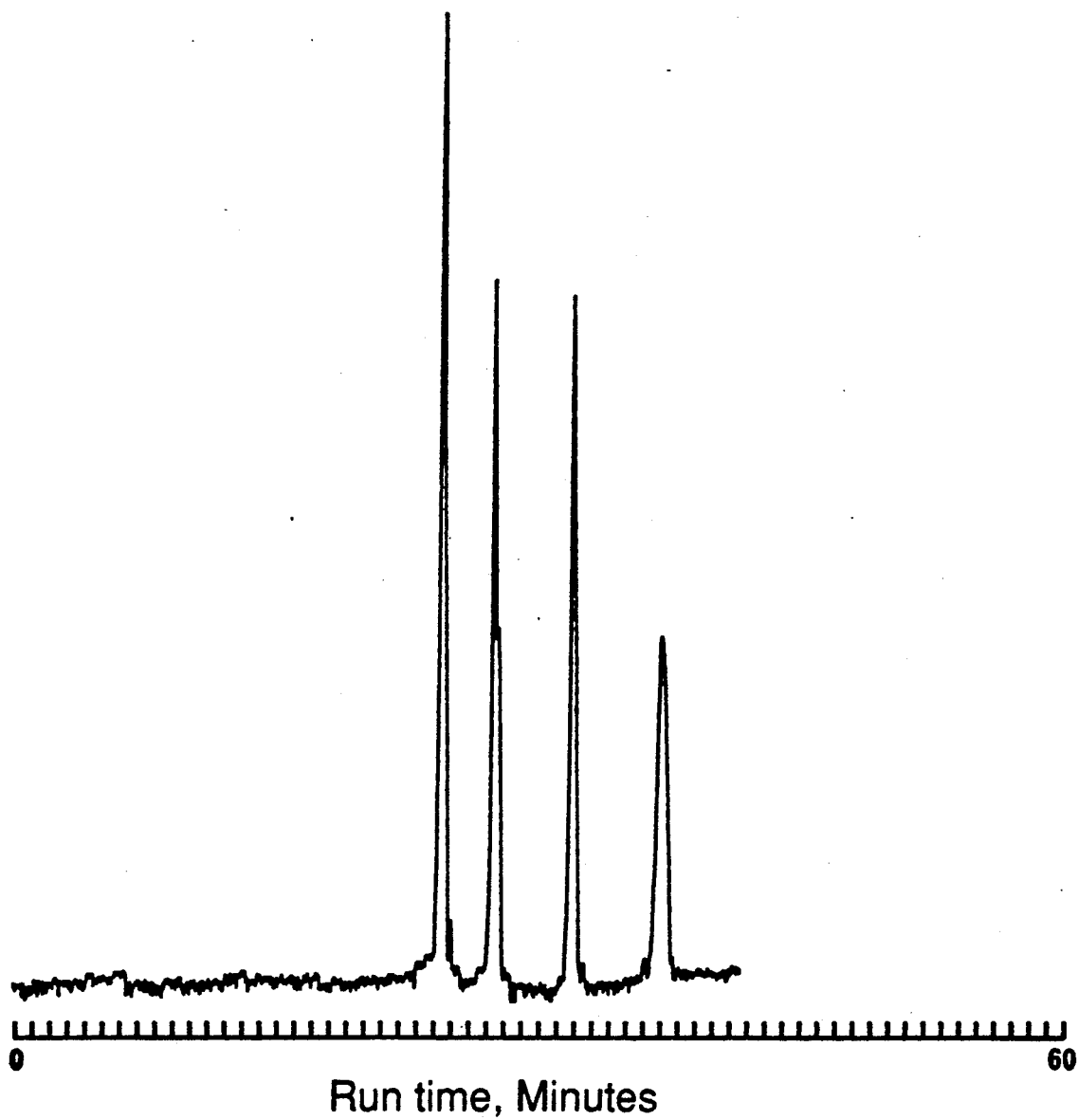
FIG. 3 shows an electrophoretic separation of the same proteins as shown in FIG. 2, under the same electrophoretic conditions except that the column used contained 7.5% total monomers.
Figure 4:
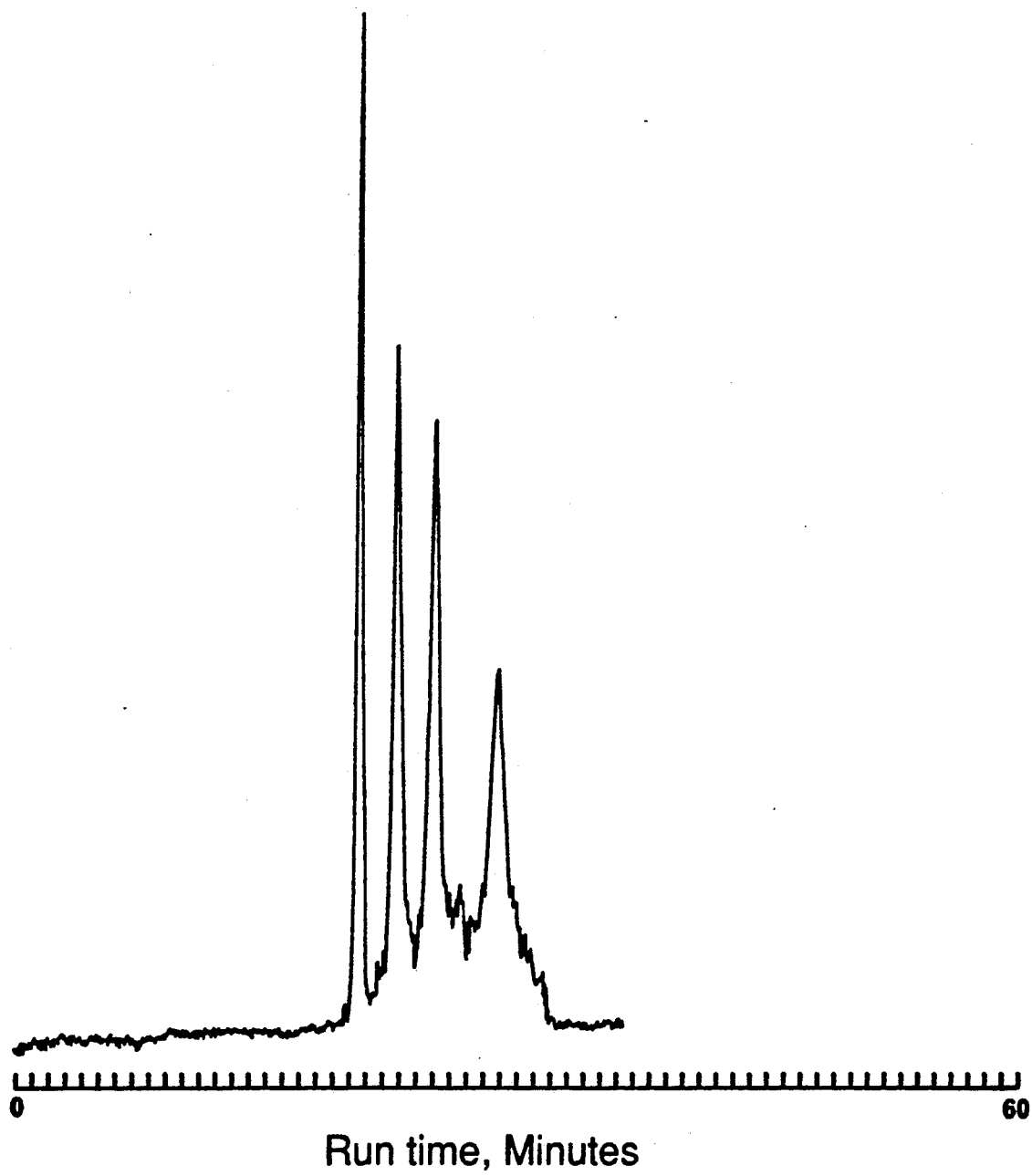
FIG. 4 shows an electrophoretic separation of the same proteins as shown in FIGS. 2 and 3, the electrophoretic conditions again being the same except that in this instance the column contained 5% total monomers.

Other microcapillary columns were prepared exactly as above, except that they possessed gels having % T=7.5% and 5%, respectively, produced by employing appropriately-diluted aliquots of the acrylamide-bisacrylamide stock solution. Mixtures of the same four proteins were separated on these microcapillary columns by electrophoresis under the same conditions as above. Results are shown in FIGS. 3 and 4 respectively.

Figure 5:
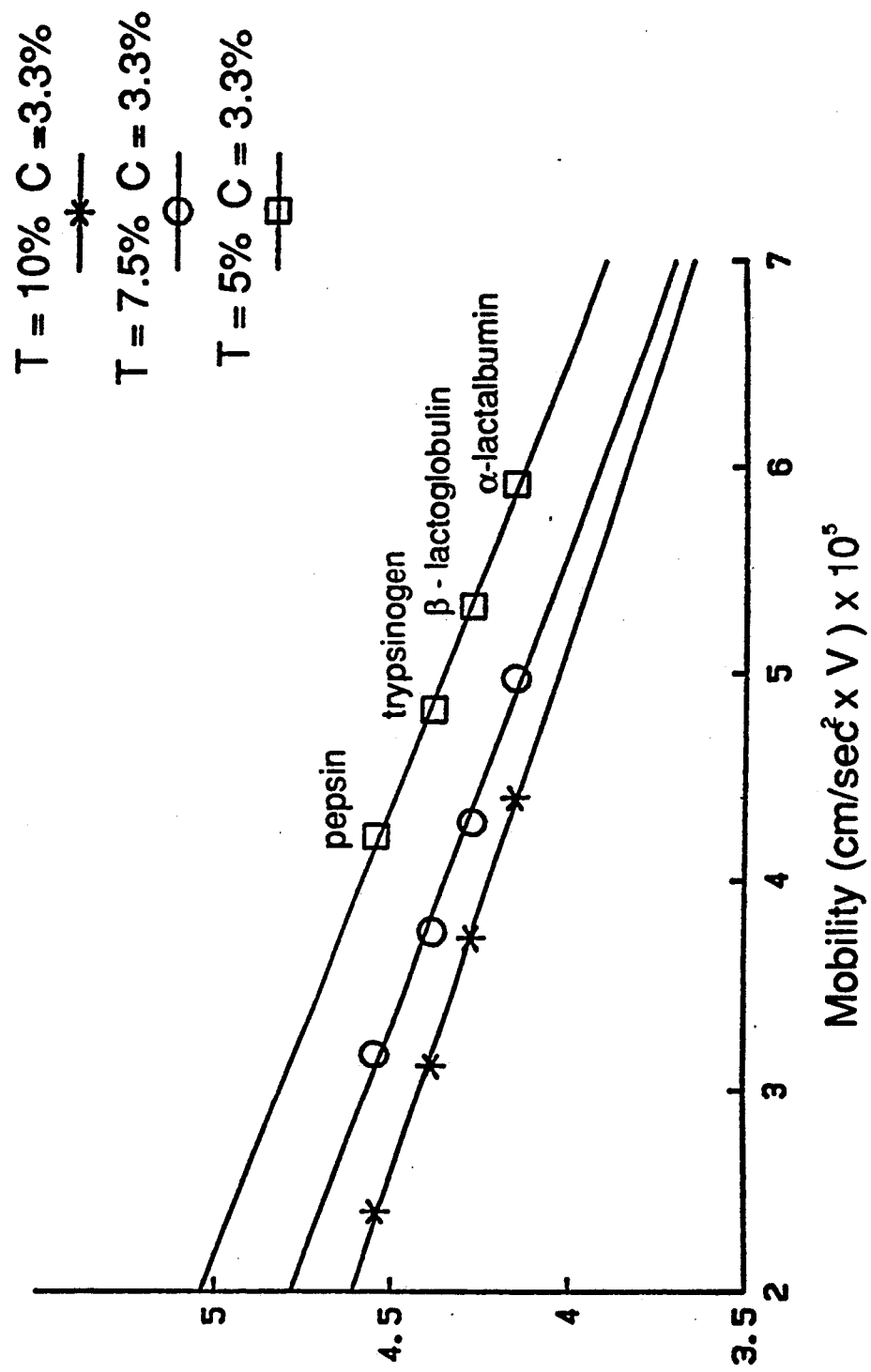
FIG. 5 shows plots of the log of the molecular weight of the tested proteins versus their mobilities on three different microcapillary gel columns of the invention.

Demonstration of Utility of the Gel-Containing Microcapillaries for Molecular Weight Determination In FIG. 5 it is shown that the logarithms of the molecular weights of the tested proteins are a linear function of their mobilities, on each of the gels tested, showing that molecular weight determinations may be performed on the gel-containing microcapillary columns of the invention.

Demonstration of Molecular Sieving

Figure 6:
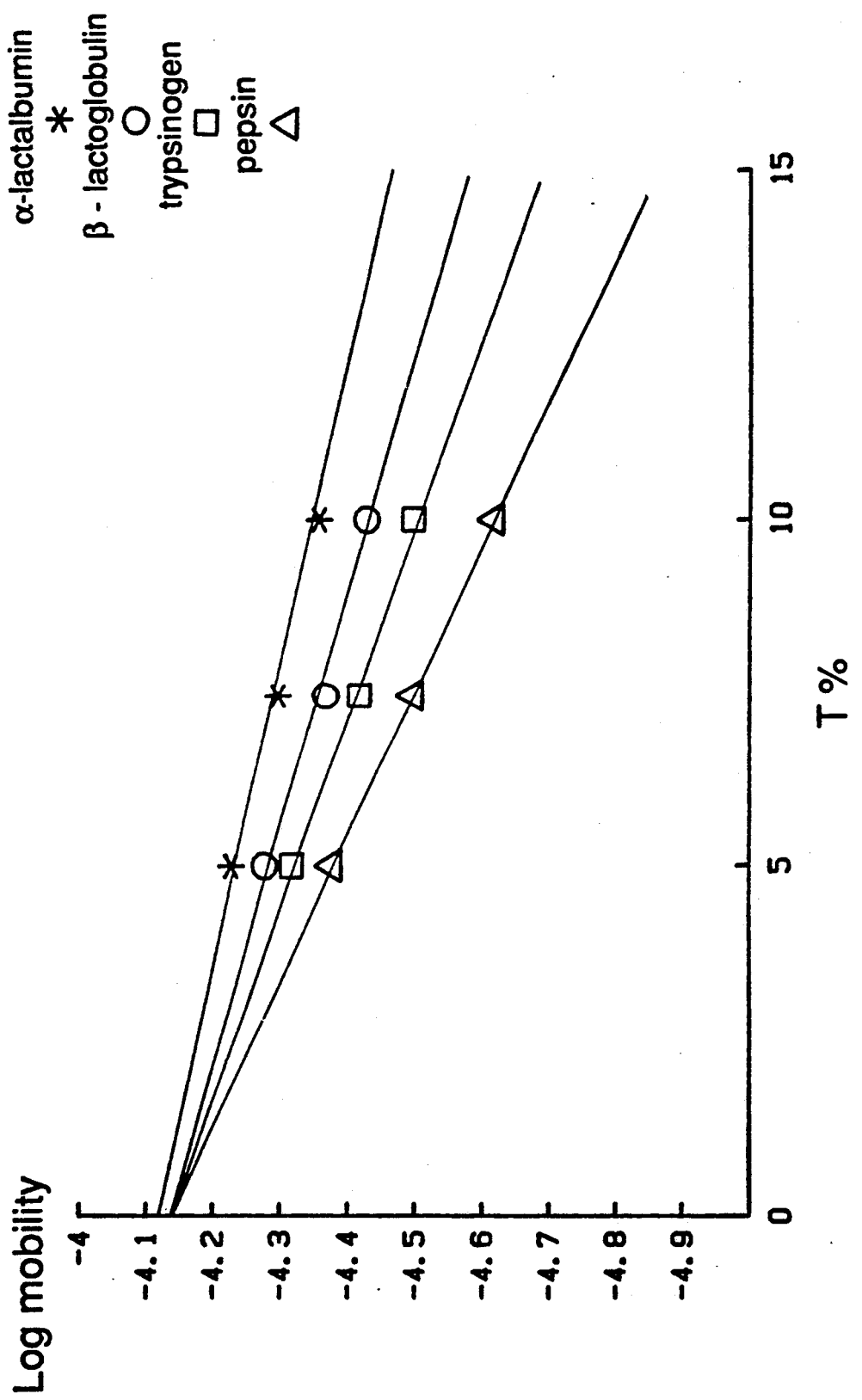
FIG. 6 shows a Ferguson plot of the data from FIGS. 2, 3, and 4.
Figure 7:
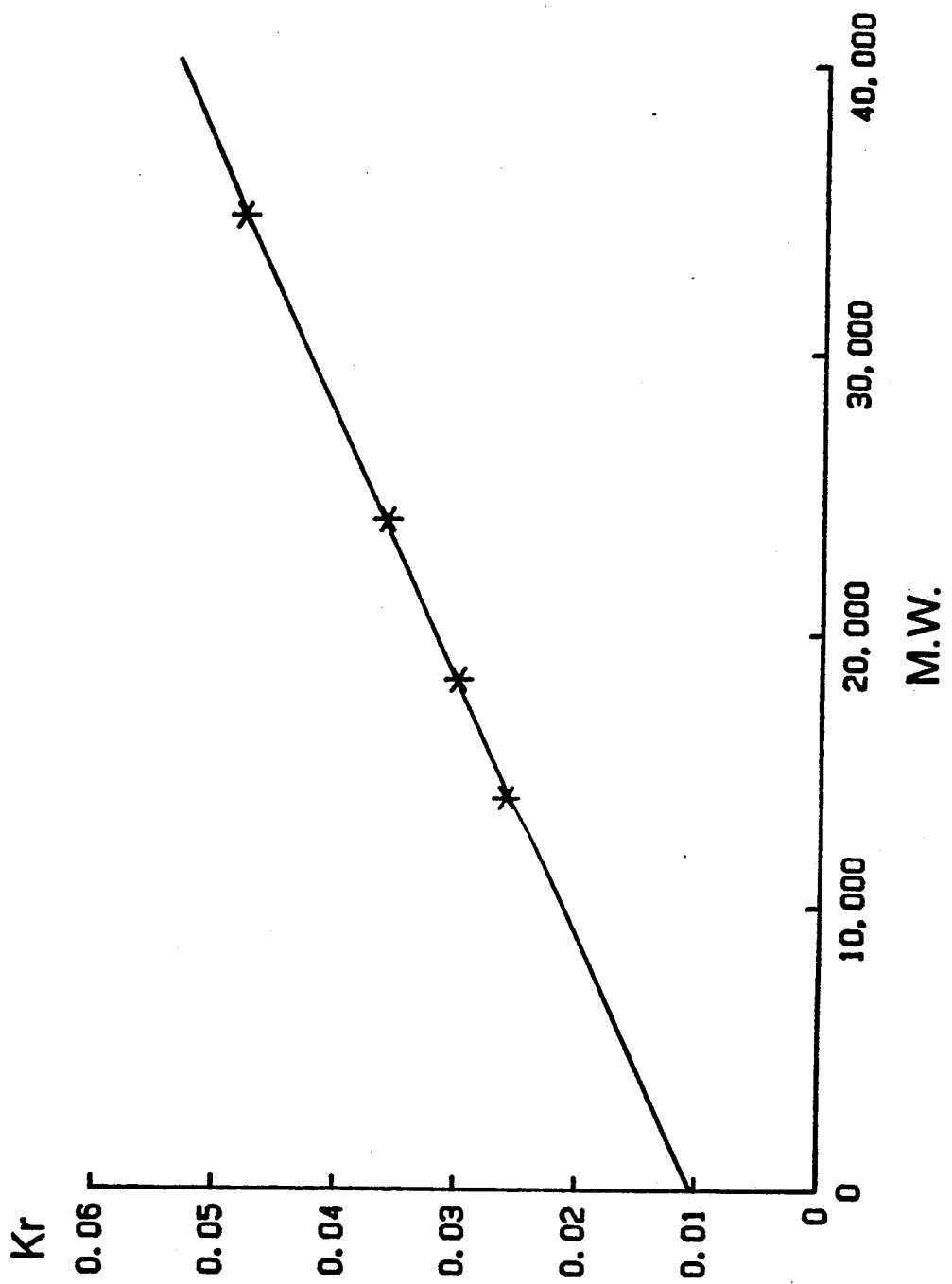
FIG. 7 shows a graph of the Ferguson plot slopes versus molecular weights of standard proteins.

In FIG. 6 the logs of the mobilities of the tested proteins on each of the tested microcapillary columns are plotted versus the % T, in a "Ferguson" plot. In accordance with the behavior expected for molecular sieving separations, the extrapolated mobilities at zero gel concentration of gel are essentially the same. In FIG. 7, the "Ferguson" plot slopes are shown to correlate linearly with the molecular weights of the separated materials, confirming utility of the gel-containing microcapillaries for molecular weight determinations.

Preparation and Testing of Gel-Containing Microcapillary Having 3% T, and 5% C

Fused silica microcapillary tubing having an ID of a polyimide coating was employed. A 40 to 45 cm length of this tubing was taken for preparation of the gel-containing microcapillary. The polyimide coating was removed from a 2 cm section of one end of the tubing by burning. This end was ultimately connected to the detector of the electrophoresis The microcapillary tubing filled with 1M KOH solution and left overnight at room temperature. Next, the microcapillary was rinsed with about twenty column volumes of a 50% solution of 3-Methacryloxypropyltrimethyoxysilane in HPLC grade methanol at room temperature. The microcapillary, filled with bifunctional reagent solution, was then plugged with septa, and left overnight.

Buffer solution was prepared by dissolving 1.1 g of TRIS buffer in 100 ml of 7 molar urea solution, adding 0.01 g of EDTA, and adjusting the pH to 8.3 by the addition of boric acid.

A solution of acrylamide and N,N'-methylenebisacrylamide was prepared by combining 19 g of acrylamide and 1 g of N,N'-methylenebisacrylamide in 100 ml of buffer solution, giving a solution having a % T of 20% and a % C of 5%.

A solution of ammonium persulfate was prepared by dissolving 0.2 g of ammonium persulfate in 2 ml of the buffer solution.

The solutions of buffer, monomers, and ammonium persulfate were separately filtered through 0.2 micrometer filters and degassed for 2 hours by applying a vacuum of 20-30 mm of mercury.

1.5 ml of the acrylamide-bisacrylamide solution was diluted to 10 ml with buffer solution, giving a final solution having % T=3% and % C=5%. This solution was filtered through a 0.2 μm filter and degassed under vacuum overnight at a vacuum of about 20-22 mm of water.

To a 0.5 ml aliquot of the acrylamide-bisacrylamide solution were added 7.5 μl of a 5% v/v solution of electrophoresis grade TEMED and 7.5 μl of 5% w/v ammonium persulfate solution, and in excess of 50 μl of this polymerization mixture was forced through the microcapillary until no bubbles were observed exiting the microcapillary. The injection syringe was carefully removed from the TEFLON tubing while continuing the injection, to prevent introduction of bubbles into the microcapillary. Finally, both ends of the microcapillary were plugged with septa and the column was placed in a refrigerator and maintained between 5° and 10° C. overnight, during which time the polymerization occurred. Finally, the front end of the microcapillary was cut off at a microcapillary migration distance (front end to detector) of 20 cm. The final gel-containing microcapillary was evaluated for one hour under an applied field of 100 volts/cm, and found to be satisfactory.

Figure 8:
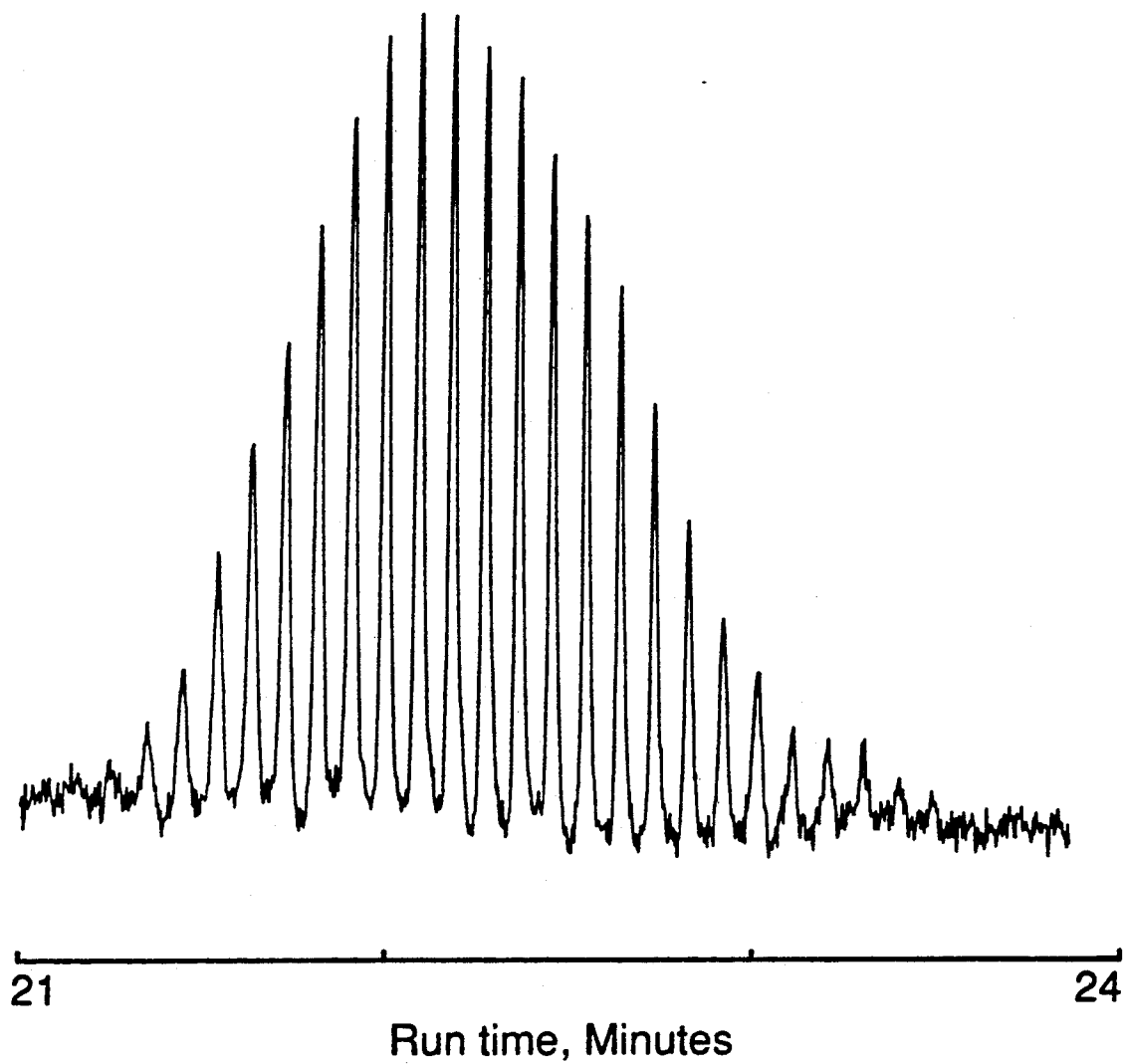
FIG. 8 shows an electropherogram of a mixture of poly(deoxyadenylic acid) oligomers, nominally of 40 to 60 bases, on a gel-containing microcapillary column of the invention containing 3% total monomer, 5% crosslinker, and no SDS. The pH of the buffer was 8.3, and electrophoresis was conducted under an applied field of 300 volts/cm and a current of 12 microamperes, over a 20 cm migration distance.

A solution of a mixture of poly(deoxyadenylic acid) oligomers of nominal 40-60 bases was electrophoretically injected onto the microcapillary column by application of an electrical field of 60 volts/cm for 5 seconds. Electrophoresis 20 cm migration distance. Results are shown in FIG. 8.

Preparation and Testing of a Gel-Containing Microcapillary Having 6% T and 0% C

Figure 9:
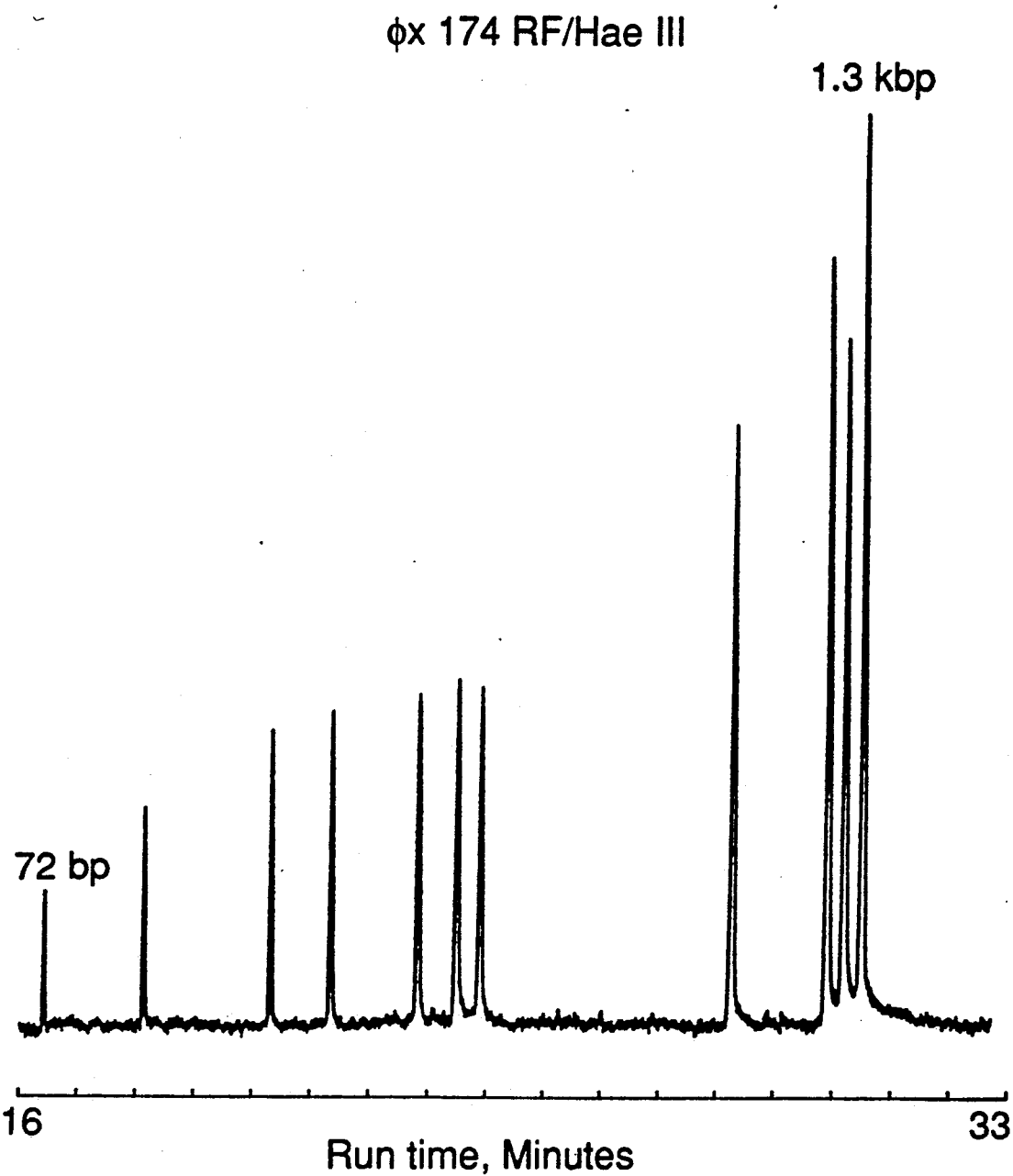
FIG. 9 shows an electropherogram of a mixture of DNA fragments of $\phi$X174RF produced by digestion with restriction enzyme Hae III. A gel-containing microcapillary column of the invention containing 6% total monomer, no crosslinker, and no SDS was used. The pH of the buffer was 8.3, and electrophoresis was conducted under an applied field of 300 volts/cm and a current of 12 microamperes, over a 20 cm migration distance.

A third microcapillary was prepared in the same manner as the 3% T and 5% C microcapillary discussed above, except that no crosslinking agent was employed and the acrylamide stock solution was prepared by combining 30 g of acrylamide in 100 ml of buffer solution, and this was diluted five fold to yield the working acrylamide solution having 6% T. A mixture of φX174RF/Hae III DNA restriction fragments ranging from 72 to 1300 base pairs was electrophoretically injected onto the microcapillary by applying a field of 60 V/cm for 10 seconds. Electrophoresis was conducted at 300 V/cm at a current of 12 microamperes over the 20 cm migration distance. Results are shown in FIG. 9.

Preparation and Testing of a Gel-Containing Microcapillary Having 6% T, 0% C, and 0.1% SDS A fourth microcapillary was prepared in the same manner as the 6% T and 0% C microcapillary discussed above, except that the buffer solution contained 0.1 g of sodium dodecyl sulfate per 100 ml, and the pH was adjusted to 7.6.

Figure 10:
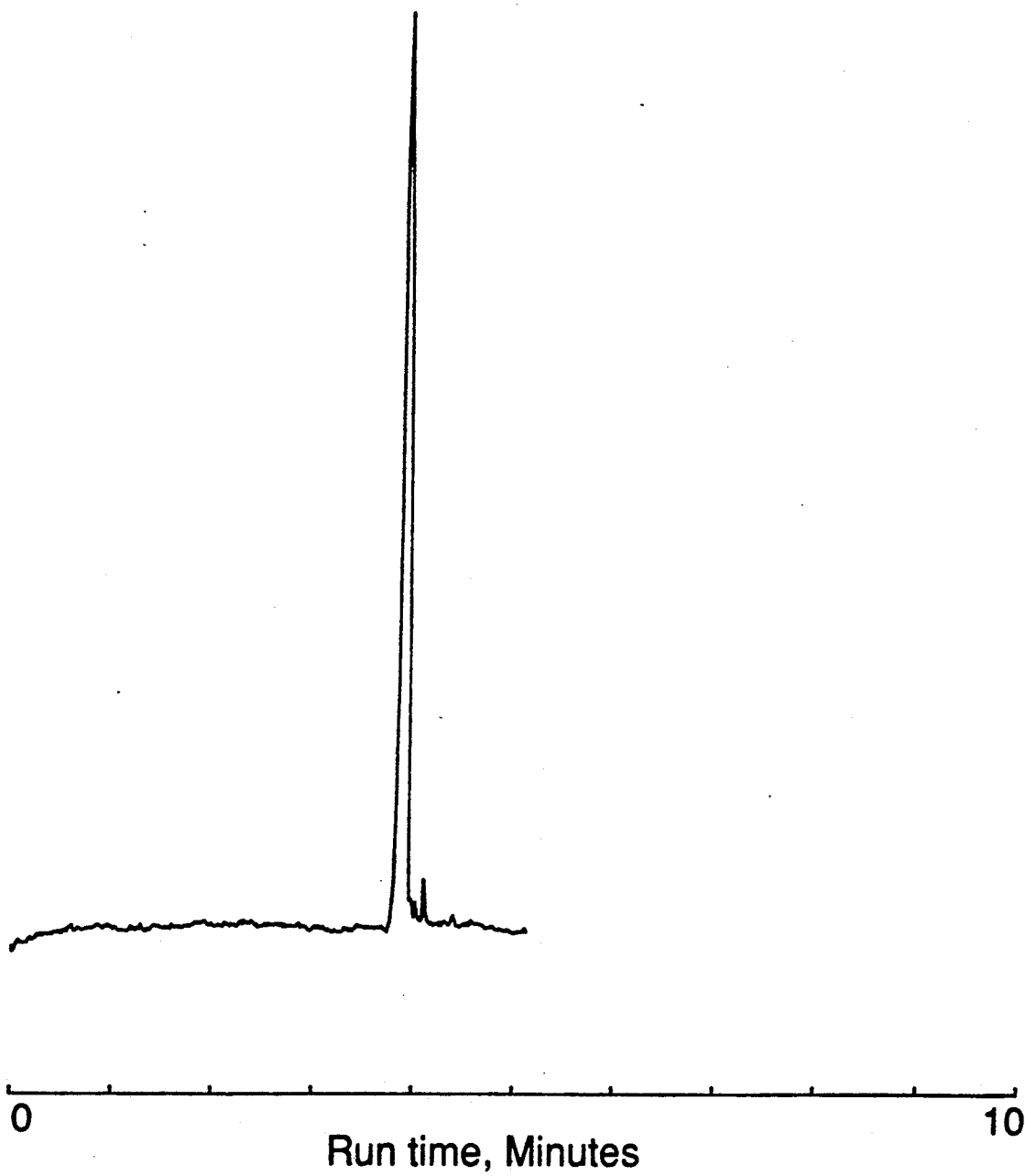
FIG. 10 shows an electropherogram of lysozyme on a gel-containing microcapillary of the invention containing 6% total monomer, no crosslinker, and 0.1% SDS. The pH of the buffer was 7.6, and electrophoresis was conducted under an applied field of 300 volts/cm and a current of 17 microamperes, over a 20 cm migration distance.

Although lysozyme has a pI greater than 11 and is therefore positively charged at pH=7.6 and expected to migrate to the negative electrode, the SDS-lysozyme complex is negatively charged and the complex therefore migrates toward the positive electrode. A solution of lysozyme was electrophoretically injected onto the microcapillary column by application of an electrical field of 60 V/cm for 15 seconds. Electrophoresis was conducted at 300 V/cm and a current of 17 microamperes over the 20 cm migration distance. Results are shown in FIG. 10.

Quality Control Testing of Microcapillary Columns

During their lifetimes, the gel-filled microcapillaries should be tested periodically for stability and reproducibility by measuring the electrophoretic current at various applied fields. Well-made columns in good condition exhibit a constant resistance over a range of applied fields and this is repeatable over time. In this test the applied field (V/cm) is plotted against the measured current. A straight line with a constant slope (resistance) over time indicates the column is good. Typical experimental data for an SDS-gel capillary column are presented in Table I below.

TABLE I

| E (V/cm) | I (μA) |
|---|---|
| 100 | 6 |
| 200 | 12 |
| 300 | 18 |
| 400 | 22 |
| 500 | 28 |
| 600 | 33 |
| 700 | 40 |

These data are indicative of a well-made column, and also demonstrate the column can be operated under an applied electric field of 700 V/cm.

Other embodiments of the invention will be apparent to those skilled in the art from a consideration of this specification or practice of the invention as disclosed herein. It is intended that the specification and examples be considered as exemplary only, with the true scope and spirit of the invention being indicated by the following claims.

What is claimed is:

1. A gel-containing microcapillary column for high precision and high performance electrophoresis, comprising:
 a microcapillary having an interior cavity and a wall with an inner surface;
 a layer of coating material covalently bonded to said inner surface of said wall; and
 a polymeric gel filling said interior cavity, said polymeric gel comprising polymerized uncrosslinked monomer.

2. The microcapillary of claim 1 wherein said microcapillary is made of fused silica.

3. The microcapillary of claim 1 wherein said polymeric gel comprises a copolymer of acrylamide.

4. The microcapillary of claim 1 wherein said coating material originates as a bifunctional reagent selected from the group consisting of 3-Methacryloxypropyl-trimethyoxysilane, 3-Methacryloxypropyldimethylethoxysilane, vinyltriacetoxysilane, vinyltri(-methoxyethoxy)silane, vinyltrichlorosilane, and methylvinyldichlorosilane.

5. A gel-containing microcapillary column for high precision high performance electrophoresis, comprising:
 a silica microcapillary having an interior cavity, a wall having an inner surface, and an internal diameter between 10 and 200 micrometers;
 a layer of coating material covalently bonded to said inner surface of said wall, said coating material being derived from 3-Methacryloxypropyl-trimethyoxysilane or 3-Methacryloxypropyldimethylethoxysilane; and
 a gel comprising uncrosslinked polyacrylamide filling said interior cavity.

6. The microcapillary of claim 5 wherein said gel is copolymer of acrylamide monomer.

7. A method of performing high resolution molecular sieving electrophoresis, comprising:

injecting an aliquot of a sample containing analytes to be separated onto a gel-containing microcapillary column comprising:

a microcapillary having an interior cavity and a wall with an inner surface;

a layer of coating material covalently bonded to said inner surface of said wall; and a polymeric gel filling said interior cavity, said polymeric gel comprising polymerized uncrosslinked monomer;

applying an electric field of at least 100 volts/cm; and instrumentally detecting and measuring the separated analytes sequentially.

* * * * *